United States Patent
Higgins et al.

(10) Patent No.: US 12,071,657 B2
(45) Date of Patent: Aug. 27, 2024

(54) NUCLEIC ACID AMPLIFICATION

(71) Applicant: Hewlett-Packard Development Company, L.P., Spring, TX (US)

(72) Inventors: Adam Higgins, Corvallis, OR (US); Pavel Kornilovich, Corvallis, OR (US); Alexander N. Govyadinov, Corvallis, OR (US); Michael J. Day, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 697 days.

(21) Appl. No.: 16/643,054

(22) PCT Filed: Oct. 20, 2017

(86) PCT No.: PCT/US2017/057672
§ 371 (c)(1),
(2) Date: Feb. 28, 2020

(87) PCT Pub. No.: WO2019/078891
PCT Pub. Date: Apr. 25, 2019

(65) Prior Publication Data
US 2020/0332342 A1 Oct. 22, 2020

(51) Int. Cl.
| | |
|---|---|
| *B01L 3/00* | (2006.01) |
| *B01L 7/00* | (2006.01) |
| *B01L 99/00* | (2010.01) |
| *C12Q 1/6806* | (2018.01) |
| *C12Q 1/686* | (2018.01) |

(52) U.S. Cl.
CPC ........ *C12Q 1/686* (2013.01); *B01L 3/502746* (2013.01); *B01L 7/525* (2013.01); *C12Q 1/6806* (2013.01); *B01L 2300/0816* (2013.01); *B01L 2300/0867* (2013.01); *B01L 2300/0883* (2013.01); *B01L 2400/0688* (2013.01); *B01L 2400/0694* (2013.01)

(58) Field of Classification Search
CPC ........... B01L 3/00; B01L 7/00; C12Q 1/6806; C12Q 1/686; C12Q 1/6844; G01N 33/53
See application file for complete search history.

(56) References Cited

U.S. PATENT DOCUMENTS

| | | |
|---|---|---|
| 5,714,380 A | 2/1998 | Neri et al. |
| 9,254,486 B2 | 2/2016 | Imran |
| 9,366,631 B2 | 6/2016 | Tan et al. |
| 2007/0111303 A1 | 5/2007 | Inoue et al. |

(Continued)

FOREIGN PATENT DOCUMENTS

| | | |
|---|---|---|
| WO | 2007028084 | 3/2007 |
| WO | 2011006671 | 1/2011 |
| WO | 2017180120 | 10/2017 |

OTHER PUBLICATIONS

Furuberg et al., RNA amplification chip with parallel microchannels and droplet positioning using capillary valves, Microsyst Technol, 14, 2008, pp. 673-681.

(Continued)

*Primary Examiner* — Lydia Edwards
(74) *Attorney, Agent, or Firm* — Foley & Lardner LLP

(57) ABSTRACT

A nucleic acid amplifier may include a sample preparation zone, a fluid ejector, an amplification zone and a capillary break between the amplification zone and the fluid ejector.

14 Claims, 7 Drawing Sheets

(56) References Cited

U.S. PATENT DOCUMENTS

| | | | |
|---|---|---|---|
| 2009/0148933 A1* | 6/2009 | Battrell | C12Q 1/686 |
| | | | 435/287.2 |
| 2012/0178091 A1* | 7/2012 | Glezer | B01L 7/525 |
| | | | 435/6.12 |
| 2016/0199839 A1 | 7/2016 | Bergstedt et al. | |
| 2016/0310948 A1 | 10/2016 | Nowakowski et al. | |

OTHER PUBLICATIONS

Roper et al., Toward an Integrated Microdevice for DNA Extraction and PCR Amplification in the Submicroliter Regime for Forensic DNA Analysis, Materials and Methods, 2007, 5 pages.
International Search Report dated Aug. 2, 2018 for PCT/US2017/057672, Applicant Hewlett-Packard Development Company, L.P.

\* cited by examiner

220 →

| 230 → | Sample Purification/Preparation Region |
| 250 → | Capillary Break |
| 240 → | Amplification Region |

304 →
Prepare/purify a sample in a first region of a microfluidic device

306 →
Direct the prepared sample to a second region of the microfluidic device

308 →
From a capillary break between the first region and the second region

310 →
Process the sample in the second region

FIG. 4

NUCLEIC ACID AMPLIFICATION

BACKGROUND

Nucleic acids, such as deoxyribonucleic acids (DNA) or ribonucleic acids (RNA), are sometimes extracted from a sample and amplified using a polymerase chain reaction or any isothermal amplification. The amplification of nucleic acids using, for example, a polymerase chain reaction may be utilized to facilitate the isolation or quantification of nucleic acids. Such amplification may offer benefits in such areas as genetic testing, tissue typing, infectious disease identification, genetic fingerprinting and the development of individually customized therapy regimens, forensic analysis, food safety, environmental testing etc.

BRIEF DESCRIPTION OF THE DRAWINGS

FIG. 3 is a schematic diagram of portions of an example nucleic acid amplifier.

FIG. 4 is a flow diagram of an example method for processing a sample.

Figure 1:
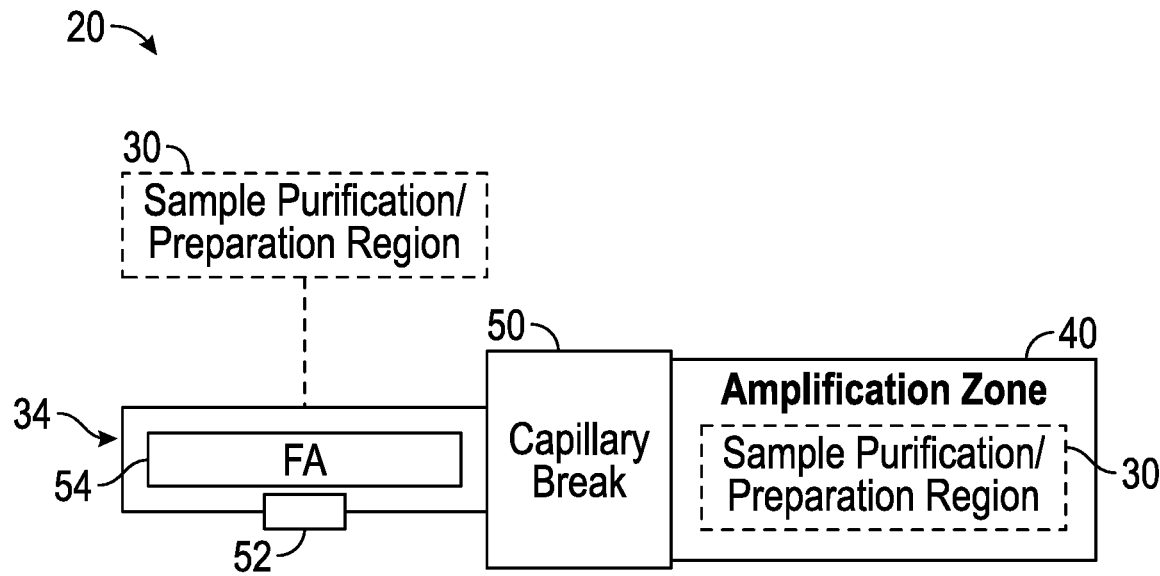
FIG. 1 is a schematic diagram of portions of an example nucleic acid amplifier.

Throughout the drawings, identical reference numbers designate similar, but not necessarily identical, elements. The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

DETAILED DESCRIPTION OF EXAMPLES

Disclosed herein are example microfluidic devices and microfluidic methods for isolating and concentrating at least one nucleic acid out of a dilute sample and amplifying the nucleic acid using, for example, a polymerase chain reaction (PCR) or an isothermal nucleic acid amplification technique. Separation and/or concentration of the nucleic acid is facilitated on the microfluidic device using fluid ejectors that eject non-nucleic acid portions of the sample through a nozzle or other orifice. Use of the fluid ejectors facilitates more rapid isolation and concentration of the nucleic acid. The concentrated nucleic acid may then be amplified with the addition of a nucleic acid amplification reagent and the application of an isothermal process or the application of PCR thermal cycling.

Isolation and concentration of the nucleic acid (sample preparation) occurs in a sample preparation zone, whereas amplification of the nucleic acid occurs in an amplification zone. The disclosed microfluidic devices and methods isolate the sample preparation zone from the amplification zone utilizing a capillary break. Once the sample has been prepared, the capillary break is broken and the isolated nucleic acid may be transported to the amplification zone.

The smaller fluid volumes processed by the microfluidic devices allow testing to be done with smaller samples and with smaller quantities of nucleic acid amplification reagent. However, in some implementations, the smaller fluid volumes may be more sensitive to fluid evaporation through the fluid ejector orifice(s). During nucleic acid amplification and thermal processing, the smaller volumes of fluid are even more susceptible to evaporation. Such evaporation, if not controlled, may result in nucleic acid amplification reagents becoming too concentrated so as to interfere with subsequent detection of the amplified nucleic acid. In some circumstances, such evaporation, if not controlled, may result in a complete loss of the volume of fluid containing the concentrated nucleic acid and the nucleic acid amplification reagent.

The disclosed microfluidic devices and methods may further address such evaporation issues by spatially separating or isolating the nozzles or orifices of the fluid ejectors from the amplification zones or regions of the microfluidic devices where the fluid containing the concentrated nucleic acid undergoes high temperatures during thermal processing. The disclosed microfluidic devices utilize a capillary break between the fluid ejectors and the amplification zone or region to provide such fluid isolation. In some implementations, a second capillary break is provided between the amplification zone and a vent, facilitating the venting of gas across the capillary break as the amplification zone is filled with the fluid containing the concentrated nucleic acid.

The use of fluid jetting and the use of a capillary break to isolate the fluid ejectors from the amplification zone facilitate rapid sample concentration and nucleic acid amplification in an integrated microfluidic device or fluidic die. The microfluidic devices may achieve nucleic acid isolation, concentration and amplification of dilute nucleic acid samples with low reagent volumes and customized, as well as complex, dispensing schemes.

The disclosed microfluidic devices and methods may employ microfluidic channels. Microfluidic channels may be formed by performing etching, microfabrication (e.g., photolithography), micromachining processes, or any combination thereof in a substrate of the fluidic die. Some example substrates may include silicon based substrates, glass based substrates, gallium arsenide based substrates, and/or other such suitable types of substrates for microfabricated devices and structures. Accordingly, microfluidic channels, chambers, orifices, and/or other such features may be defined by surfaces fabricated in the substrate of a fluidic die. Furthermore, as used herein a microfluidic channel may correspond to a channel of sufficiently small size (e.g., of nanometer sized scale, micrometer sized scale, millimeter sized scale, etc.) to facilitate conveyance of small volumes of fluid (e.g., picoliter scale, nanoliter scale, microliter scale, milliliter scale, etc.).

Example microfluidic devices or dies described herein may comprise microfluidic channels in which fluidic actuators may be disposed. In such implementations, actuation of a fluid actuator disposed in a microfluidic channel may generate fluid displacement in the microfluidic channel. The fluid actuators may include a piezoelectric membrane based actuator, a thermal resistor based actuator, an electrostatic membrane actuator, a mechanical/impact driven membrane actuator, an electrochemical actuator, a magneto-strictive drive actuator, or other such elements that may cause displacement of fluid responsive to electrical actuation.

Disclosed herein is a nucleic acid amplifier that comprises a sample preparation zone, a fluid ejector, an amplification zone and a capillary break between the amplification zone and the fluid ejector. Disclosed herein is an example nucleic acid amplifier that has a sample preparation zone and an amplification zone separated by a capillary break.

Disclosed herein is an example method nucleic acid amplification method that comprises isolating a nucleic acid from non-nucleic acid portions of a sample, ejecting the non-nucleic acid portions of the sample through an orifice with a fluid actuator, applying a fluid to the isolated nucleic acid, adding a nucleic acid amplification reagent to the fluid and heating the fluid with the isolated nucleic acid and the nucleic acid amplification reagent in a thermal processing region separated from the orifice by a capillary break.

FIG. 1 is a schematic diagram of an example nucleic acid amplifier 20. Nucleic acid amplifier 20 is part of a microfluidic device or a microfluidic die that carries out nucleic acid isolation and concentration from a dilute sample and that further amplifies the concentrated nucleic acid by applying PCR or any isothermal amplification. Nucleic acid amplifier 20 utilizes a fluid ejector to facilitate more rapid isolation and concentration of the nucleic acid out of the dilute sample. Nucleic acid amplifier 20 utilizes a capillary break to separate the fluid ejector from an amplification zone, controlling or inhibiting the flow of fluid into the amplification zone while the sample is being prepared. In some applications, the capillary break additionally controls or limits evaporation during thermal cycling. Nucleic acid amplifier 20 comprises sample purification/preparation zone 30, fluid ejector 34, amplification zone 40 and capillary break 50.

Sample purification/preparation zone 30 comprises a region of amplifier 20 that carries out the preparation and purification of the sample to isolate a nucleic acid portion of a sample from non-nucleic acid portions of a dilute sample. The separated or isolated nucleic acid is retained within the purification/preparation zone while the non-nucleic acid portions of the dilute sample are flushed or otherwise removed by fluid ejector 34.

In one implementation, region 30 comprises a region to contain nucleic acid adsorption beads and retaining structures that inhibit such adsorption beads from passing to fluid ejector 34. For example, in one implementation, sample purification/preparation zone 30 may comprise pillars or posts arranged or spaced apart from one another so as to inhibit such adsorption beads from passing to fluid ejector 34. In one implementation, the adsorption beads are provided as part of amplifier 20, contained within region 30 prior to the receipt of a sample that potentially contains a nucleic acid. In another implementation, the adsorption beads are added to the sample prior to the sample being placed within region 30.

In other implementations, other structures or processes may be utilized to isolate and concentrate the nucleic acid from the non-nucleic acid portions of a dilute sample. For example, in other implementations, region 30 may comprise an embedded grid like or fiber like filter to which the nucleic acid selectively adheres or an embedded membrane. In yet other implementations, such as where the sample contains few bacteria or a small percentage of non-nucleic acid elements, separation may be omitted, wherein the nucleic acid may be concentrated by evaporation.

As indicated by broken lines, sample purification is preparation zone 30 is fluidly coupled to fluid ejector 34. The term "fluidly coupled" shall mean that two or more fluid transmitting volumes are connected directly to one another or are connected to one another by intermediate volumes or spaces such that fluid may flow from one volume into the other volume. In one implementation, region 30 is directly coupled to fluid ejector 34. In one implementation, fluid ejector 34 is adjacent to or contained within region 30.

Fluid ejector 34 comprise a device to selectively eject fluid, such as fluid containing non-nucleic acid portions of the sample, out of region 30. In one implementation, fluid ejector 34 may eject such fluid to a diaper or other waste reservoir. In the example illustrated, fluid ejector 34 comprises orifice 52 and fluid actuator 54. Orifice 52 comprise an opening through which the ejected fluid passes. Orifice 52 may be in the form of a nozzle or nozzle opening. Fluid actuator 54 comprises a component that displaces fluid through orifice 52. The fluid actuator 54 may include a piezoelectric membrane based actuator, a thermal resistor based actuator, an electrostatic membrane actuator, a mechanical/impact driven membrane actuator, an electrochemical actuator, a magneto-strictive drive actuator, or other such elements that may cause displacement of fluid responsive to electrical actuation. Although amplifier 20 is illustrated as comprising a single fluid ejector 34, it should be appreciated that amplifier 20 may include multiple fluid ejectors 34 to increase the rate at which nucleic acids in a dilute sample may be concentrated.

Amplification zone 40 comprises a volume or portion of amplifier 20 in which the isolated and concentrated nucleic acid, produced in region 30, is amplified through the process of PCR or isothermal amplification. For such nucleic acid amplification, the isolated and concentrated nucleic acid is combined with a nucleic acid amplification reagent, sometimes referred to as a master mix, which comprises a heat stable nucleic acid polymerase, such as Taq polymerase. The nucleic acid amplification reagent may further comprise primers such as short nucleic acid fragments (nucleic acid oligonucleotides) that contain sequences complementary to the target nucleic acid to be amplified. The nucleic acid amplification reagent may comprise other elements as well such as (1) deoxynucleotide triphosphates, or dNTPs (nucleotides containing triphosphate groups), the building blocks from which the DNA polymerase synthesizes a new DNA strand; (2) a buffer solution providing a suitable chemical environment for activity and stability of the nucleic acid polymerase; (3) bivalent cations, such as magnesium (Mg) or manganese (Mn) ions (Mg2+ or Mn2+); and (4) monovalent cations, such as potassium (K+) ions.

In one implementation, the nucleic acid amplification reagent is added to the isolated and concentrated nucleic acid within zone 40. In another implementation, the nucleic acid amplification reagent is added to the isolated and concentrated nucleic acid prior to the nucleic acid being deposited or directed into zone 40. In some implementations, the nucleic acid amplification reagent may be freeze-dried in microfluidic passages or reservoirs of amplifier 20, wherein the nucleic acid amplification reagent mixes with a fluid containing the nucleic acid prior to entering the amplification zone 40. In yet other implementations, the nucleic acid amplification reagent is pre-supplied to zone 40, awaiting the arrival of the nucleic acid. For example, in one implementation, the nucleic acid amplification reagent is freeze-dried within amplification zone 40, ready for the arrival of a fluid containing the nucleic acid.

To carry out nucleic acid amplification, amplification zone 40 facilitates thermal cycling of the mixture of the concentrated nucleic acid and the nucleic acid amplification reagent. In one implementation, amplification zone 40 comprises at least one heater which may be selectively controlled to heat the mixture pursuant to an isothermal amplification process or PCR. For example, in one implementation amplification zone 40 may comprise at least one thermal resistor that outputs heat in response to being supplied with electrical current. In other implementations, amplification zone 40 may comprise other types of heaters. In yet other implementations, amplification zone 40 may include or be located adjacent to a thermally conductive surface, wherein at least one external heater is utilized to selectively heat the thermally conductive surface to carry out the thermal cycling.

Capillary break 50 extends between and separates amplification zone 40 from the orifice 52 of fluid ejector 34. Capillary break 50 may be formed by a constriction dimensioned such that a capillary meniscus forms between or along a gas-liquid interface. The capillary meniscus inhibits the flow of fluid across or through the constriction until the meniscus is broken in response to pressure of the liquid at the gas-liquid interface exceeding a pressure threshold that depends upon characteristics of the constriction as well as the gas and liquid on either side of the interface. During amplification, the fluid mixture containing the nucleic acid and the nucleic acid amplification reagents is subjected to high heat which may cause high rates of evaporation. In some implementations, capillary break 50 reduces such evaporation by separating and isolating amplification zone 40 from orifice 52 of fluid ejector 34.

Figure 2:
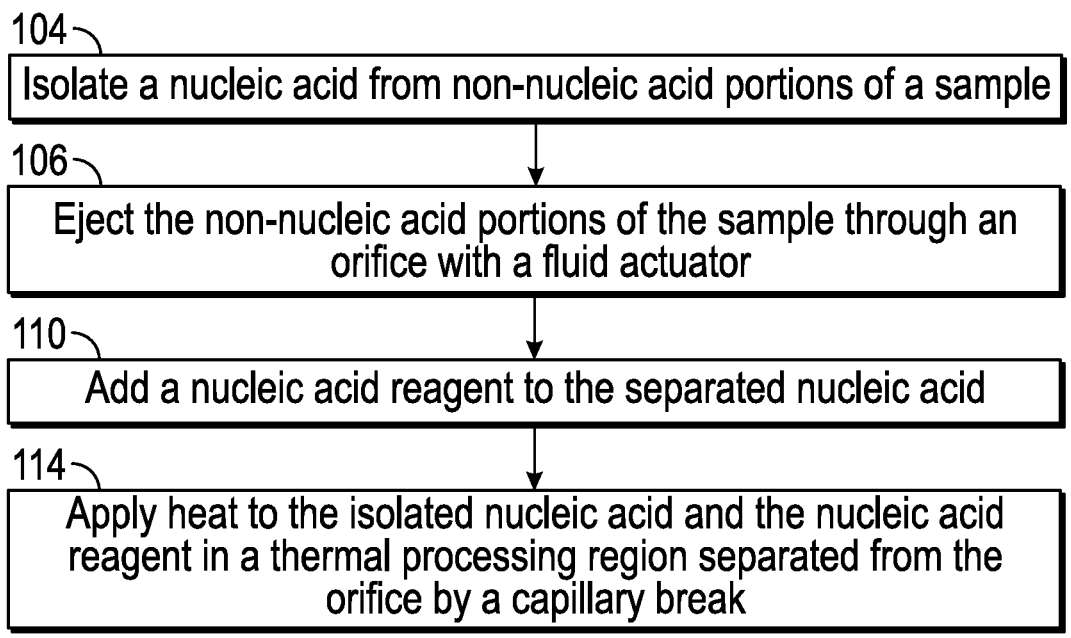
FIG. 2 is a flow diagram of an example nucleic acid amplification method.

FIG. 2 is a flow diagram of an example nucleic acid amplification method 100. Method 100 facilitates the use of a microfluidic die or device to both isolate and concentrate a nucleic acid out of a dilute sample and amplify the nucleic acid using PCR. Method 100 facilitates isolation and concentration of the nucleic acid out of a dilute sample while reducing evaporation that might otherwise occur during heating of the sample as the nucleic acid is amplified. Although method 100 is described as being carried out by amplifier 20, it should be understood that method 100 may likewise be carried out with any of the amplifiers described herein that comprise a fluid ejector or other amplifiers that utilize a fluid ejector to eject fluid.

As indicated by block 104, a nucleic acid is isolated from non-nucleic acid portions of a sample. In amplifier 20, such isolation occurs within region 30. In one implementation, the nucleic acid may be isolated from non-nucleic acid portions of the sample with nucleic acid adsorption beads to which the targeted nucleic acid adsorbs while the remaining untargeted portions of the sample remain with the fluid of the sample. In another implementation, the nucleic acid may be isolated from non-nucleic acid portion of the sample with the use of a filter or membrane.

As indicated by block 106, the non-nucleic acid portions of the sample are ejected through an orifice by a fluid actuator of a fluid ejector. As described above with respect to amplifier 20, the non-nucleic acid portions of the sample may be ejected to a diaper or reservoir. The non-nucleic acid portions of the sample may be ejected utilizing a fluid ejector having a fluid actuator that may include a piezoelectric membrane based actuator, a thermal resistor based actuator, an electrostatic membrane actuator, a mechanical/impact driven membrane actuator, an electrochemical actuator, a magneto-strictive drive actuator, or other such elements that may cause displacement of fluid responsive to electrical actuation. In some implementations, multiple fluid ejectors may be utilized to enhance the rate at which the sample is purified/prepared.

In some implementations, the fluid ejector may be further utilized to eject a washing or cleaning solution or fluid. While the nucleic acid remains adsorbs to adsorption beads or other structures, those portions of the preparation zone 30 may be washed or cleaned with a cleaning fluid which is ejected through orifice 52 by fluid actuator 54. This may be performed to further increase the likelihood that the non-nucleic acid portion of the sample are removed with respect to the separated and isolated target nucleic acid.

As indicated by block 110, a nucleic acid amplification reagent may be added to the separated or isolated nucleic acid. In one implementation, the nucleic acid amplification reagent is part of a fluid that is applied to the isolated nucleic acid. In another implementation, a fluid may first be added to the nucleic acid and then the mixture of the fluid and nucleic acid be combined with the nucleic acid amplification reagent. In some implementations, the nucleic acid amplification reagent may be freeze-dried prior to being added to the fluid containing the isolated nucleic acid.

As indicated by block 114, heat is applied to the fluid with the isolated nucleic acid and the nucleic acid amplification reagent to amplify the nucleic acid. In some implementations, the heat is applied as part of an isothermal amplification process. In some implementations, heat is applied as part of a thermal cycling process, such as with PCR. In each of such implementations, the amplification zone where heat is applied is separated from the preparation zone and the orifice by a capillary break. The capillary break may be formed by a constriction dimensioned such that a capillary meniscus forms between or along a gas-liquid interface. The capillary meniscus inhibits the flow of fluid across or through the constriction until the meniscus is broken in response to pressure of the liquid at the gas-liquid interface exceeding a pressure threshold that depends upon characteristics of the constriction as well as the gas and liquid on either side of the interface.

During the application of heat and amplification, the fluid mixture containing the nucleic acid and the nucleic acid amplification reagents is subjected to high heat which may cause high rates of evaporation. In some implementations, the capillary break reduces such evaporation by separating and isolating the thermal cycling region from the orifice.

FIG. 3 is a schematic diagram illustrating another example nucleic acid amplifier 220. Nucleic acid amplifier 220 comprises sample purification/preparation zone 230, amplification zone 240 and capillary break 250. Sample purification/preparation zone 230 comprises a region of amplifier 220 that carries out the preparation and purification of the sample to isolate a nucleic acid portion of a sample from non-nucleic acid portions of a dilute sample. The separated or isolated nucleic acid is retained within the purification/preparation zone while the non-nucleic acid portions of the dilute sample are flushed or otherwise removed by a fluid ejector. In one implementation, region 230 is similar to region 30 described above.

Amplification zone 240 is similar to amplification zone 40 described above. Amplification zone 240 comprises a volume or portion of amplifier 20 in which the isolated and concentrate nucleic acid, produced in region 30, is amplified through the application of heat, whether as part of an isothermal amplification process or a PCR thermal cycling process. As described above, amplification zone 240 facilitates heating of the mixture of the isolated or concentrated nucleic acid produced in region 230 and the nucleic acid amplification reagent. As described above, in some implementations, the nucleic acid amplification reagent may be added to the nucleic acid before the nucleic acid enters amplification zone on 40 or after the nucleic acid enters amplification zone 240. In some implementations, the nucleic acid amplification reagent may be freeze-dried in region 240 or in other volumes of amplifier 220 that lead to region 240.

Capillary break 250 extends between and isolates sample purification preparation zone 230 and amplification zone 240. Capillary break 250 is similar to capillary break 50 described above in that capillary break 250 may be formed by a constriction dimensioned such that a capillary meniscus forms between or along a gas-liquid interface. The constriction reduces an area of the liquid-gas interface where evaporation may occur while the capillary meniscus inhibits the flow of fluid across or through the constriction until the meniscus is broken in response to pressure of the liquid at the gas-liquid interface exceeding a pressure threshold that depends upon characteristics of the constriction as well as the gas and liquid on either side of the interface. In some implementations, capillary break 250 may further reduce evaporation of the fluid within amplification region 240 that might otherwise occur through openings provided in region 230, such as orifices or fluid ejector openings, vents, fill openings or the like.

FIG. 4 is a flow diagram of an example method 300 for processing a fluid sample, wherein the sample undergoes two separate processes in separate zones. For example, method 300 may be utilized to process a fluid sample, wherein the fluid sample undergoes preparation in a first region or zone and undergoes amplification in a second region or zone. Method 300 utilizes a capillary break to separate and isolate two different processing regions of an integrated microfluidic device. Although method 300 is specifically described in the context of nucleic acid amplification where fluid undergoes heating in an amplification zone that is isolated from a purification/preparation zone by a capillary break, it should be appreciated that method 300 may likewise be carried out in other fluid processes carried out on microfluidic devices where fluid is differently treated in two different zones.

As indicated by block 304, a fluid sample is prepared and/or purified in a first region of a microfluidic device, such as in a first region of a microfluidic die. The first region may be fluidly connected to or may include openings or orifices through which vapors resulting from evaporation may escape, further enhancing subsequent evaporation of the fluid. For example, the first region may include a fill opening through which the fluid is deposited into the first region from the outside, vents or nozzles through which fluid is ejected by fluid actuator.

In one implementation, a nucleic acid may be isolated and concentrated from a dilute sample in the first region, such as region 230 of amplifier 220 as described above. As described above with amplifier 220, the first region is fluidly connected to a fluid ejector 34. In another implementation, the fluid may be prepared in other fashions depending upon the processing protocol being followed.

As indicated by block 306, once prepared, the fluid is directed to a second region of the microfluidic device or die. The second region may be a region where the fluid undergoes a process that increases the rate of evaporation of the fluid. For example, amplifier 220 comprise an amplification zone 240 where the fluid undergoes thermal cycling, subjecting the fluid to heat that increase the rate of evaporation of the fluid.

As indicated by block 308, a capillary break is formed between the first region and the second region. In one implementation, the prepared sample is directed to the second region (in block 306) after the capillary break has been formed, wherein the capillary break is temporarily broken to allow the prepared sample to move into the second region, wherein the capillary break is reestablished once the prepared sample has entered the second region. In another implementation, the capillary break is initially formed once the prepared sample has entered the second region.

As indicated by block 310, sample is processed in the second region. Such processing occurs while the capillary break isolates a second region from the first region, isolating the fluid in the second region from the openings or orifices in the first region. In particular implementations where method 300 is a PCR amplification, such processing involves thermal cycling of the fluid in the second region. In other implementations, the processing of sample and the second region may involve other processes performed on the sample, such other heating protocols or processes.

Figure 5:
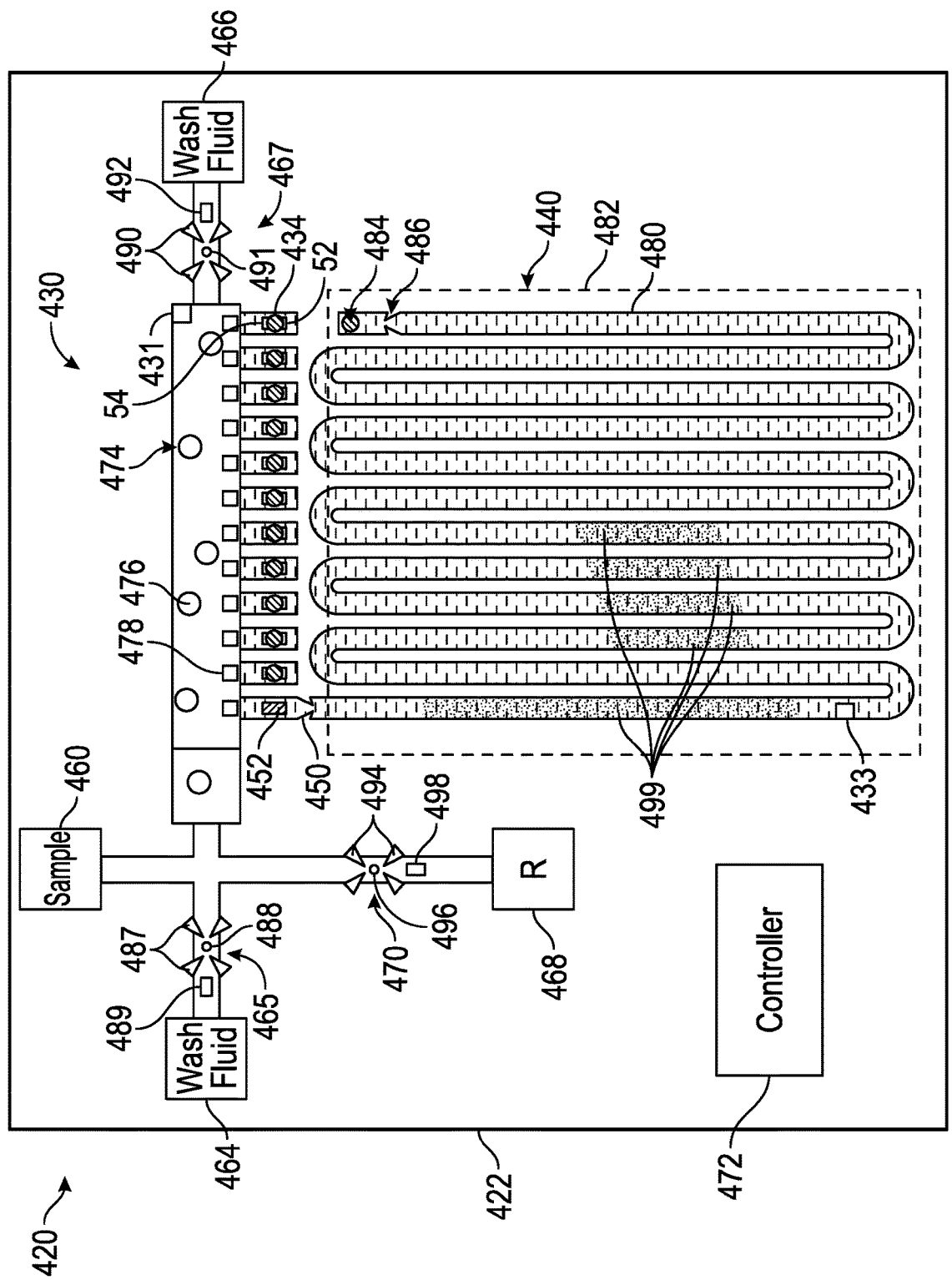
FIG. 5 is a schematic diagram of portions of an example nucleic acid amplifier.

FIG. 5 schematically illustrates portions of an example nucleic acid amplifier 420. Amplifier 420 comprises substrate 422, sample purification/preparation zone 430, fluid ejectors 434, nucleic acid amplification zone 440, capillary break 450, capillary break opener 452, sample supply 460, wash fluid supply 464, wash fluid valve 465, elution fluid supply 466, elution fluid valve 467, nucleic acid amplification reagent supply 468, nucleic acid amplification reagent valve 470 and controller 472.

Substrate 422 comprises a base or foundation upon which the remaining components of amplifier 420 are formed so as to provide an integrated microfluidic die for carrying out nucleic acid isolation, concentration and amplification. In one implementation, substrate 422 may comprise silicon, in some implementations, substrate 422 may be composed of multiple materials, wherein microfluidic channels or passages as well as microfluidic reservoirs formed in substrate 422 are formed from an epoxy resin or photoresist material such as SU8. In other implementations, substrate 422 may comprise silicon based substrates, glass based substrates, gallium arsenide based substrates, and/or other such suitable types of substrates for, wherein microfluidic channels may be formed by performing etching, microfabrication (e.g., photolithography), micromachining processes, or any combination thereof. Components supported by substrate 422 may be controlled and provided with electrical power through electrically conductive traces or wires formed upon a carried upon substrate 422 and connected to controller 472 as well as power sources (not shown).

Sample purification/preparation zone 430 is similar to zone 30 described above except that zone 430 is specifically illustrated as being in the form of a slot comprising nucleic acid separator 474. Nucleic acid separator 474 separates and isolates nucleic acid from non-nucleic acid portions of a dilute sample using nucleic acid adsorption beads 476 (a portion of which are schematically shown) and adsorption bead retainers 478. Nucleic acid adsorption beads 476 are formed from material or are coated such that a target nucleic acid absorbs to the beads 476. As described above, the nucleic acid adsorption beads 476 may reside within zone 430 prior to the addition of a dilute sample or maybe added to the dilute sample prior to the introduction of the dilute sample into zone 430. Nucleic acid adsorption bead retainers 478 inhibit the passage of beads 476 (and the absorbed target nucleic acid) from zone 430 to fluid ejectors 434. In the example illustrated, retainers 478 comprise pillars or posts between zone 430 and the microfluidic passages or chambers containing fluid ejectors 434. In other implementations, retainers 478 may comprise other forms of a filter which block the passage of beads 476 while permitting the fluid containing non-nucleic acid portions to pass therethrough to fluid ejectors 434.

In yet other implementations, nucleic acid separator 474 may have other forms. For example, in other implementations, nucleic acid separator 474 may comprise a mesh or other filtering material that adsorbs targeted nucleic acids. In yet other implementations, nucleic acid separator may comprise an embedded membrane. In some implementations, nucleic acid separator 474 may be omitted such as where the diluted sample includes few bacteria such that the nucleic acid may be concentrated through evaporation.

Fluid ejectors 434 dispenses or ejects the non-nucleic acid portions of the dilute sample separated from the target nucleic acid. Fluid ejectors 434 are fluidly connected to sample preparation zone 430. Each of fluid ejectors 434 comprises an orifice 52 and a fluid actuator 54 (described above).

Nucleic acid amplification zone 440 is to carry out thermal cycling and amplification of the isolated and concentrated nucleic acid output by sample preparation zone 430. Nucleic acid amplification zone 440 comprises thermal processing (thermal cycling or isothermal) region 480, heater 482, vent 484, capillary break 484. Thermal processing region 480 comprises the region that receives the isolated and concentrated nucleic acid output by sample preparation zone 430. In the example illustrated, thermal processing region 480 comprises a serpentine microfluidic passage for containing the nucleic acid and the nucleic acid amplification reagent as they undergo thermal processing. In other implementations, nucleic acid amplification zone 440 may have other shapes.

Thermal processing region 480 is associated with heater 482, wherein the nucleic acid along with a nucleic acid amplification reagent undergoes heating to amplify or multiply the nucleic acid. In one implementation, heater 482 comprises at least one thermal resistor formed in substrate 422 which outputs heat to region 480. In PCR amplification processes, the heat output by heater 44 is varied to carry out PCR thermal cycling.

Vent 484 comprises an opening in fluid communication or fluidly coupled to thermal processing region 480. Vent 484 discharges air from thermal processing region 480, facilitating the inflow of the concentrated nucleic acid into the serpentine passage of thermal processing region 480. In other implementations, the shape of the microfluidic passage may vary and may consist of array of small connected chambers or one big reservoir or any other configuration Capillary break 486 extends between and isolates thermal processing region 480 and vent 484. Capillary break 486 is similar to capillary break 50 described above in that capillary break 486 may be formed by a constriction dimensioned such that a capillary meniscus forms between or along a gas-liquid interface. The constriction reduces an area of the liquid-gas interface where evaporation may occur while the capillary meniscus inhibits the flow of fluid across or through the constriction until the meniscus is broken in response to pressure of the liquid at the gas-liquid interface exceeding a pressure threshold that depends upon characteristics of the constriction as well as the gas and liquid on either side of the interface.

Capillary break 450 extends between and isolates sample preparation zone 430 and thermal processing region 480 of amplification zone 440. Capillary break 450 is similar to capillary break 50 described above in that capillary break 450 may be formed by a constriction dimensioned such that a capillary meniscus forms between or along a gas-liquid interface. The constriction reduces an area of the liquid-gas interface where evaporation may occur while the capillary meniscus inhibits the flow of fluid across or through the constriction until the meniscus is broken in response to pressure of the liquid at the gas-liquid interface exceeding a pressure threshold that depends upon characteristics of the constriction as well as the gas and liquid on either side of the interface.

Capillary break opener 452 selectively and controllably opens capillary break 450 to facilitate the flow of fluid into thermal processing region 480. Capillary break opener 452 comprises a device or component to create a fluid pressure differential across the gas-liquid interface of the meniscus of capillary break 450 to break the meniscus. In the example illustrated, capillary break opener 452 comprises a fluid actuator that displaces fluid to increase the pressure of the fluid to an extent sufficient to break the meniscus across capillary break 450. The fluid actuator may include a piezo-electric membrane based actuator, a thermal resistor based actuator, an electrostatic membrane actuator, a mechanical/impact driven membrane actuator, a magneto-strictive drive actuator, an electrochemical actuator, or other such elements that may cause displacement of fluid responsive to electrical actuation. In other implementations, the capillary break opener 452 may comprise a heater that heats the fluid to a sufficient extent so as to break the capillary meniscus.

Sample supply 460 comprises a region of microfluidic die 422 for the supply of the dilute sample containing or potentially conveying the nucleic acid to be amplified. Sample supply 460 is fluidly connected to sample preparation zone 430. In one implementation, sample supply 460 comprises a reservoir containing the sample. In another implementation, sample supply 460 comprises an inlet port through which the sample may be introduced to amplifier 420.

Wash fluid supply 464 comprises a region of microfluidic die 422 for the supply of a wash fluid. The wash fluid comprises a fluid that serves as a solvent or other fluid that rinses surfaces of nucleic acid separator 474, such as adsorption beads 476, and cleans them from non-nucleic acid contaminants. Wash fluid supply 464 is fluidly connected to sample preparation zone 430. In one implementation, wash fluid supply 464 comprises a reservoir containing the wash fluid. In another implementation, wash fluid supply 464 comprises an inlet port through which the wash fluid may be introduced to amplifier 420.

Wash fluid valve 465 selectively controls the flow of wash fluid from wash fluid supply 464 to sample preparation zone 430. In the example illustrated, wash fluid valve 465 comprises capillary breaks 487, vent 488 and capillary break opener 489. Capillary breaks 487 are similar to capillary breaks 450 and 484 in structure and function. Capillary breaks 487 form a pair of consecutive capillary breaks, reducing the likelihood of valve 465 accidentally opening. Each capillary break 487 comprises a constriction sized such that a meniscus forms at a gas-liquid interface across the constriction. Vent 488 comprise an opening adjacent and between the constrictions. Vent 488 vents gas from between the capillary breaks as the capillary breaks are being broken by capillary break opener 489.

Capillary break opener 489 selectively and controllably opens capillary breaks 487 to facilitate the flow of fluid into sample preparation zone 430. Capillary break opener 489 is similar capillary break opener 452. Capillary break opener 489 comprises a device or component to create a fluid pressure differential across the gas-liquid interface of the meniscus of capillary break 487 to consecutively break the menisci. In the example illustrated, capillary break opener 489 comprises a fluid actuator that displaces fluid to increase the pressure of the fluid to an extent sufficient to break the meniscus across capillary breaks 487. The fluid actuator may include a piezoelectric membrane based actuator, a thermal resistor based actuator, an electrostatic membrane actuator, a mechanical/impact driven membrane actuator, a magnetostrictive drive actuator, an electrochemical actuator, or other such elements that may cause displacement of fluid responsive to electrical actuation. In other implementations, the capillary break opener 489 may comprise a heater that heats the fluid to a sufficient extent so as to break the capillary meniscus.

Elution fluid supply 466 comprises a region of microfluidic die 422 for the supply of an elution fluid. The elution fluid comprises a fluid that serves as a solvent or other fluid that carries the concentrated nucleic acid into amplification zone 440. In implementations where nucleic acid adsorption beads are utilized to separate and isolate the nucleic acid from the dilute sample in preparation zone 430, the elution fluid removes or elutes the nucleic acid from the beads and transports the nucleic acid from the preparation zone 430 to the amplification zone 440.

Elution fluid supply 466 is fluidly connected to sample preparation zone 430. In one implementation, elution fluid supply 466 comprises a reservoir containing the wash fluid. In another implementation, elution fluid supply 466 comprises an inlet port through which the elution fluid may be introduced to amplifier 420.

Elution fluid valve 467 selectively controls the flow of elution fluid from elution fluid supply 466 to sample preparation zone 430. In the example illustrated, elution fluid valve 467 comprises capillary breaks 490, vent 491 and capillary break opener 492. Capillary breaks 490 are similar to capillary breaks 450 and 487 in structure and function. Capillary breaks 490 form a pair of consecutive capillary breaks, reducing the likelihood of valve 467 accidentally opening. Each capillary break 490 comprises a constriction sized such that a meniscus forms at a gas-liquid interface across the constriction. Vent 491 comprise an opening adjacent and between the constrictions. Vent 491 vents gas from between the capillary breaks as the capillary breaks are being broken by capillary break opener 492.

Capillary break opener 492 selectively and controllably opens capillary breaks 490 to facilitate the flow of fluid into sample preparation zone 430. Capillary break opener 492 is similar capillary break opener 452. Capillary break opener 492 comprises a device or component to create a fluid pressure differential across the gas-liquid interface of the meniscus of capillary breaks 490 to consecutively break the menisci. In the example illustrated, capillary break opener 492 comprises a fluid actuator that displaces fluid to increase the pressure of the fluid to an extent sufficient to break the meniscus across capillary breaks 490. The fluid actuator may include a piezoelectric membrane based actuator, a thermal resistor based actuator, an electrostatic membrane actuator, a mechanical/impact driven membrane actuator, a magnetostrictive drive actuator, an electrochemical actuator, or other such elements that may cause displacement of fluid responsive to electrical actuation. In other implementations, the capillary break opener 492 may comprise a heater that heats the fluid to a sufficient extent so as to break the capillary meniscus. In implementations where the nucleic acid amplification reagent comprises an elution fluid for eluting the nucleic acid from separator 474, such as from beads 476, and transporting the nucleic acid to the amplification zone 440, elution fluid supply 466 and elution fluid valve 467 may be omitted.

Nucleic acid amplification reagent (R) supply 468 comprises a region of microfluidic die 422 for the supply of a nucleic acid amplification reagent. The nucleic acid amplification reagent, sometimes referred to as a master mix, comprises a heat stable nucleic acid polymerase, such as Taq polymerase. The nucleic acid amplification reagent may further comprise primers such as short nucleic acid fragments (nucleic acid oligonucleotides) that contain sequences complementary to the target nucleic acid to be amplified. The nucleic acid amplification reagent may further comprise other elements as well such as (1) deoxynucleotide triphosphates, or dNTPs (nucleotides containing triphosphate groups), the building blocks from which the DNA polymerase synthesizes a new DNA strand; (2) a buffer solution providing a suitable chemical environment for activity and stability of the nucleic acid polymerase; (3) bivalent cations, such as magnesium (Mg) or manganese (Mn) ions (Mg2+ or Mn2+); and (4) monovalent cations, such as potassium (K+) ions.

Nucleic acid amplification reagent supply 468 is fluidly connected to sample preparation zone 430. In one implementation, nucleic acid amplification reagent supply 468 comprises a reservoir containing the reagent fluid. In another implementation, amplification reagent supply 468 comprises an inlet port through which the reagent may be introduced to amplifier 420.

Nucleic acid amplification reagent valve 470 selectively controls the flow of the reagent fluid from nucleic acid amplification reagent supply 468 to sample preparation zone 430. In the example illustrated, nucleic acid amplification reagent valve 470 comprises capillary breaks 494, vent 496 and capillary break opener 498. Capillary breaks 494 are similar to capillary breaks 450 and 484 in structure and function except that capillary breaks 494 comprise a pair of consecutive capillary breaks, reducing the likelihood of valve 470 accidentally opening. Each capillary break 494 comprises a constriction sized such that a meniscus forms at a gas-liquid interface across the constriction. Vent 496 comprises an opening adjacent and between the constrictions. Vent 496 vents gas from between the capillary breaks as the capillary breaks are being broken by capillary break opener 498.

Capillary break opener 498 selectively and controllably opens capillary breaks 494 to facilitate the flow of fluid into sample preparation zone 430. Capillary break opener 498 is similar capillary break opener 452. Capillary break opener 498 comprises a device or component to create a fluid pressure differential across the gas-liquid interface of the meniscus of each of capillary breaks 494 to consecutively break the menisci. In the example illustrated, capillary break opener 498 comprises a fluid actuator that displaces fluid to increase the pressure of the fluid to an extent sufficient to break the meniscus across capillary breaks 494. The fluid actuator may include a piezoelectric membrane based actuator, a thermal resistor based actuator, an electrostatic membrane actuator, a mechanical/impact driven membrane actuator, a magneto-strictive drive actuator, an electrochemical actuator, or other such elements that may cause displacement of fluid responsive to electrical actuation. In other implementations, the capillary break opener 498 may comprise a heater that heats the fluid to a sufficient extent so as to break the capillary meniscus.

In the example illustrated, amplifier 420 utilizes nucleic acid amplification reagent supply 468 and nucleic acid amplification reagent valve 470 to selectively supply the nucleic acid amplification reagent to the nucleic acid being amplified. In one implementation, the nucleic acid amplification reagent is supplied to the concentrated nucleic acid, carried by the fluid from supply 466, prior to the mixture fluid entering amplification zone 440. In another implementation, the nucleic acid amplification reagent is supplied to the concentrated nucleic acid, carried by the fluid from supply 466, after the fluid has entered the amplification zone 440.

In some implementations, amplifier 420 may comprise a freeze-dried nucleic acid amplification reagent 499 within amplification region 480. In one implementation, the freeze-dried nucleic acid amplification reagent 499 contained within amplification region 480 of amplification zone 440 may comprise a complete mixture of amplification enhancing materials. For example, the freeze-dried PCR rated 499 may comprise a heat stable nucleic acid polymerase, such as Taq polymerase. The nucleic acid amplification reagent 499 may further comprise primers such as short nucleic acid fragments (nucleic acid oligonucleotides) that contain sequences complementary to the target nucleic acid to be amplified. The nucleic acid amplification reagent 499 may further comprise other elements as well such as (1) deoxynucleoside triphosphates, or dNTPs, the building blocks from which the DNA polymerase synthesizes a new DNA strand; (2) a buffer solution providing a suitable chemical environment for activity and stability of the nucleic acid polymerase; (3) bivalent cations, such as magnesium (Mg) or manganese (Mn) ions (Mg2+ or Mn2+); and (4) monovalent cations, such as potassium (K+) ions. In some implementations, the various components or elements of the nucleic acid amplification reagent 499 may be consecutively or sequentially located along amplification region 480 to provide a staged addition of such chemicals or biological material to the fluid carrying or potentially carrying the concentrated nucleic acid.

In one implementation, the freeze-dried nucleic acid amplification reagent 499 may supplement the nucleic acid amplification reagent supplied through or by supply 468. In another implementation, supply 468 and valve 470 may be omitted. In one implementation, the freeze-dried nucleic acid amplification reagent 499 may comprise a first portion of the set of chemicals or biological materials for PCR amplification while supply 468 provides a second distinct portion of the set of chemicals or biological materials for PCR amplification. For example, in one implementation, those chemical elements that may be more suited to freeze-drying or that may be more suited to wetting may be freeze-dried in amplification region 480 while other chemical elements or biological materials less suited to freeze-drying may be provided through supply 468.

Controller 472 comprises a processing unit and associated instructions that control at least some of the functions carried out on die 422. The processing unit of controller 472 follows such instructions, contained on a non-transitory computer-readable medium, to control fluid actuators 54, to control capillary break opener 489, capillary break opener 496 and capillary break opener 452. The processing unit of controller 472 is connected to each of such component through electrically conductive wires or traces on die 422.

In one implementation, controller 472 carries out method 100 described above. In one implementation, controller 472 receives an input indicating when a sample has been introduced into sample preparation zone 430. In other implementations, controller 472 is connected to a sensor 431 that senses the introduction of a sample into sample preparation zone 430. Following a predetermined lapse of time sufficient to allow nucleic acid separation, isolation and concentration, such as adsorption to beads 476 in one implementation, controller 472 outputs control signals causing actuators 54 to eject non-nucleic acid portions into a diaper, reservoir or another passage.

In one implementation, the sample introduced by sample supply 460 comprises cells that have undergone lysis. In another implementation, the cells in the sample undergo lysis within sample preparation zone 430. For example, cells of the sample may undergo chemical lysis, such as with surfactants, in sample preparation zone 430.

Upon receiving an input or signal from sensor 431 indicating that the non-nucleic acid portions of the sample have been sufficiently ejected and discharged, controller 472 may output control signals causing capillary break opener 489 to break the menisci of capillary breaks 487 to open valve 465, supplying the wash fluid from supply 464 to sample preparation zone 430. In one implementation, the introduction of the wash fluid 464 may be sensed by sensor 431 and communicated to controller 472. The wash fluid further ensures removal of non-nucleic acid portions of the sample. Controller 472 may output control signals causing fluid actuators 54 to further eject the wash fluid through orifices 52. The wash cycle may be repeated until the preparation zone 430 has been sufficiently washed and cleaned and is emptied.

Following the cleaning of sample preparation zone 430, controller 472 may further output control signals causing capillary break opener 492 to open valve 467, supplying the elution fluid from supply 466 to sample preparation zone 430. The elution fluid releases or elutes the nucleic acid from any nucleic acid retainers/filters/beads. In one implementation, the fluid releases the nucleic acid from the adsorption beads 476.

Upon the release of the nucleic acid from the retainers, such as beads 476, controller 472 outputs control signals causing capillary break opener 498 to open valve 470, supplying a fluid containing the nucleic acid amplification reagent from supply 468 to sample preparation zone 430. The nucleic acid amplification reagent fluid mixes with the nucleic acid in sample preparation zone 430. In implementations where the reagent fluid has a composition so as to release or elutes the nucleic acid from any nucleic acid retainers/filters, such as from the adsorption beads 476, the supplying of the elution fluid from supply 466 through the actuation of valves 467 may be omitted.

As noted above, in some implementations, the step may be modified or omitted where amplification region 480 includes freeze-dried nucleic acid amplification reagent 499. In such an implementation, the fluid (provided from supply 468, from sample supply 460 or another port or reservoir) may omit nucleic acid amplification reagent, wherein the fluid releases a nucleic acid and carries a nucleic acid into amplification region 480 where the fluid then mixes with the freeze-dried nucleic acid amplification reagent. The volume of the fluid, whether containing nucleic acid amplification reagent or omitting nucleic acid amplification reagents, is controlled so as to substantially, and in one implementation fully, prime amplification region 480 without opening or breaking meniscus across capillary break 486.

Upon mixing of the nucleic acid amplification reagent with the released nucleic acid in preparation zone 430, as determined from signals from sensor 431, controller 472 outputs control signals actuating capillary break opener 452. In one implementation, controller 472 outputs control signals actuating a fluid actuator so as to break the meniscus across capillary break 450, facilitating the flow of fluid mixture containing the nucleic acid amplification reagent and the nucleic acid into amplification region 480. In one implementation, sample preparation zone 430 is backfilled with fluid, such as with water, to further inhibit evaporation during thermal cycling.

Upon mixing of the nucleic acid amplification reagent (whether from supply 468 and/or from freeze-dried reagent 499), controller 472 may output control such signals causing heater 482 to heat or thermal cycle the fluid mixture within amplification region 480. In some implementations, controller 472 may comprise at least one sensor 433, located within amplification region 480, which indicates to controller 472 the presence of the fluid mixture in amplification region 480, its state of amplification and/or the current temperature of the fluid mixture. During such isothermal heating or thermal cycling, evaporation from the amplification region 480 is reduced as there are very few vent ports. The meniscus across capillary break 486 reduces evaporation through vent 484 whereas the meniscus across capillary break 450, reestablished after priming of the amplification region 480, reduces evaporation through orifices 52.

Upon completion of the heating or thermal cycling, the presence and amount, if any, of the targeted nucleic acid is sensed or detected. In one implementation, microfluidic die 422 comprises a window or transparent portions that facilitate optical sensing or detection of the targeted nucleic acid within amplification region 480. The amplification carried out by amplifier 420 may be utilized to facilitate the isolation or quantification of nucleic acids. Such amplification may offer benefits in such areas as genetic testing, tissue typing, infectious disease identification, genetic fingerprinting and the development of individually customized therapy regimens.

Figure 6:
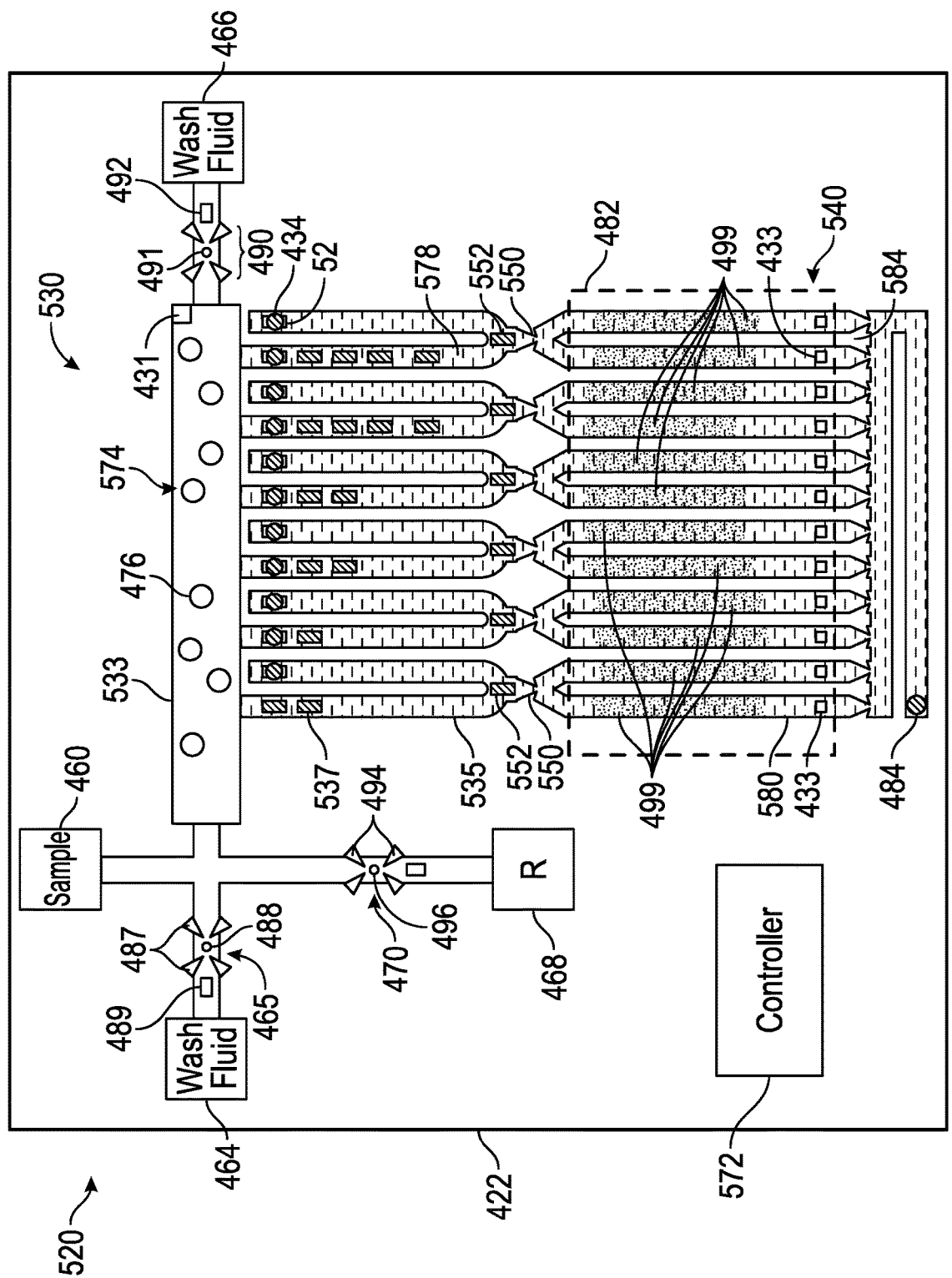
FIG. 6 is a schematic diagram of portions of an example nucleic acid amplifier.

FIG. 6 schematically illustrates portions of an example nucleic acid amplifier 520. Nucleic acid amplifier 520 comprises substrate 422, sample purification/preparation zone 530, fluid ejectors 434, nucleic acid amplification zone 540, capillary breaks 550, capillary break openers 552, sample supply 460, wash fluid supply 464, wash fluid valve 465, elution fluid supply 466, elution fluid valve 467, nucleic acid amplification reagent supply 468, nucleic acid amplification reagent valve 470 and controller 572. Those components of amplifier 520 which correspond to components of amplifier for 20 are numbered similarly.

Sample purification/preparation zone 530 comprises an area of microfluidic die 422 where a targeted nucleic acid is separated or isolated from remaining non-nucleic acid portions of a sample introduced through sample supply 460. In the example illustrated, zone 430 comprises an elongate slot 533, a series of U-shaped microfluidic passages 535, nucleic acid separator 574 and cell lysers 537. Slot 533 is connected to sample supply 460, wash fluid supply 464 and nucleic acid amplification reagent supply 468. Microfluidic passages 535 have one end connected to slot 533 and a second opposite terminal end containing fluid ejectors 434.

Nucleic acid separator 574 separator isolates nucleic acid from non-nucleic acid portions of a dilute sample. In one implementation, nucleic acid separator 574 comprises nucleic acid adsorption beads 476 (a portion of which are schematically shown) and adsorption bead retainers 578. Nucleic acid adsorption beads 476 are formed from material or are coated such that a target nucleic acid adsorbs to the beads 476. Nucleic acid adsorption beads 476 may reside within zone 430 prior to the addition of a dilute sample or may be added to the dilute sample prior to the introduction of the dilute sample into zone 430. Nucleic acid adsorption beads 476 are retained in slot 533 and/or passages 535 by retainers 578.

Nucleic acid adsorption bead retainers 578 inhibit the passage of beads 476 (and the absorbed target nucleic acid) from zone 430 to fluid ejectors 434. In the example illustrated, retainers 578 comprise pillars or posts within passages 535, between slot 533 and fluid ejectors 434. In other implementations, retainers 478 may comprise other forms of a filter which block the passage of beads 476 while permitting the fluid containing non-nucleic acid portions to pass therethrough to fluid ejectors 434.

In yet other implementations, nucleic acid separator 574 may have other forms. For example, in other implementations, nucleic acid separator 574 may comprise a mesh or other filtering material that adsorbs targeted nucleic acids. In yet other implementations, nucleic acid separator may comprise an embedded membrane. In some implementations, nucleic acid separator 574 may be omitted such as where the diluted sample includes few bacteria such that the nucleic acid may be concentrated through evaporation.

Fluid ejectors 434 dispense or eject the non-nucleic acid portions of the dilute sample separated from the target nucleic acid. Fluid ejectors 434 reside at the end of passages 535, with retainers 578 positioned between fluid ejectors 434 and slot 533. Each of fluid ejectors 434 comprises an orifice 52 and a fluid actuator 54 (described above).

Cell lysers 537 comprise components supported by microfluidic die 422 for lysing the cells contained within the sample introduced through sample supply 460. Cell lysers 537 apply heat and/or agitation to the lysate the cells. In the example illustrated, cell lysers 537 comprise fluid actuators that agitate the fluid. In one implementation, cell lysers 537 comprise thermal resistive fluid actuators that agitate as well as heat the fluid to lyse the cells of the sample. The fluid actuators forming cell lysers 537 are sequentially or serially located along each of passages 535 between slot 533 and retainers 578. As shown by FIG. 6, the number of cell lysers may vary. The multiple cell lysers 537 sequentially located along each of passages 535 facilitate staged lysing of the cells, wherein the different cell lysers along each individual passage 535 may have different characteristics or may be actuated in different manners by controller 572 depending upon the relative location of the individual cell lysers in the series along each passage 535. In one implementation, the cell lysers are simultaneously actuated or fired. In another implementation, the cell lysers are sequentially actuated or fired.

Nucleic acid amplification zone 540 is to carry out thermal cycling and amplification of the isolated and concentrated nucleic acid output by sample preparation zone 530. Nucleic acid amplification zone 540 comprises thermal processing regions 580, heater(s) 482, vent 484 and capillary breaks 586. Thermal processing regions 580 comprise individual and distinct microfluidic passages that receive the isolated and concentrated nucleic acid output by sample preparation zone 530. In other implementations, thermal processing region 580 may have other shapes.

Each thermal processing region 580 is associated with a heater 482, wherein the nucleic acid along with a nucleic acid amplification reagent undergoes thermal cycling to amplify or multiply the nucleic acid. In one implementation, heater 482 comprises at least one thermal resistor formed in substrate 422 which outputs heat to region 480. The heat output by heater 482 may be isothermal in nature or may be varied to carry out PCR thermal cycling. In one implementation, each of such regions 580 comprise a dedicated heater, wherein the different heaters may be operated independent of one another to perform different thermal cycling in the different regions. In another implementation, such regions 580 share a single heater.

Vent 484 comprises an opening in fluid communication or fluidly coupled to thermal cycling regions 580. Vent 484 discharges air from thermal cycling regions 580, facilitating the inflow of the concentrated nucleic acid into the different thermal cycling regions 580.

Capillary breaks 586 extend between and isolates their respective thermal cycling regions 580 and vent 44. Capillary break 584 is similar to capillary break 50 described above in that capillary break 586 may be formed by a constriction dimensioned such that a capillary meniscus forms between or along a gas-liquid interface. The constriction reduces an area of the liquid-gas interface where evaporation may occur while the capillary meniscus inhibits the flow of fluid across or through the constriction until the meniscus is broken in response to pressure of the liquid at the gas-liquid interface exceeding a pressure threshold that depends upon characteristics of the constriction as well as the gas and liquid on either side of the interface.

Capillary breaks 550 extend between and isolates sample preparation zone 430 and thermal processing regions 580 of amplification zone 540. Capillary breaks 550 are each similar to capillary break 50 described above in that each capillary break 550 may be formed by a constriction dimensioned such that a capillary meniscus forms between or along a gas-liquid interface. The constriction reduces an area of the liquid-gas interface where evaporation may occur while the capillary meniscus inhibits the flow of fluid across or through the constriction until the meniscus is broken in response to pressure of the liquid at the gas-liquid interface exceeding a pressure threshold that depends upon characteristics of the constriction as well as the gas and liquid on either side of the interface.

Capillary break openers 552 selectively and controllably open their respective capillary breaks 550 to facilitate the flow of fluid into the respective thermal processing region 580. Capillary break openers 552 each comprise a device or component to create a fluid pressure differential across the gas-liquid interface of the meniscus of capillary break 550 to break the meniscus. In the example illustrated, each capillary break opener 552 comprises a fluid actuator that displaces fluid to increase the pressure of the fluid to an extent sufficient to break the meniscus across capillary break 550. The fluid actuator may include a piezoelectric membrane based actuator, a thermal resistor based actuator, an electrostatic membrane actuator, a mechanical/impact driven membrane actuator, a magneto-strictive drive actuator, an electrochemical actuator, or other such elements that may cause displacement of fluid responsive to electrical actuation. In other implementations, the capillary break openers 552 may comprise a heater that heats the fluid to a sufficient extent so as to break the capillary meniscus.

In some implementations, capillary break openers 552 may be omitted, wherein cell lysers 537 also serve as capillary break openers. For example, in some implementations, the meniscus at each of capillary breaks 550 may be maintained by actuating fluid ejectors 434 concurrently with the actuation of firing of cell lysers 537, such that any pressure increase is insufficient so as to break the meniscus across capillary breaks 550. To break the meniscus across capillary breaks 550 to allow fluid to flow into amplification regions 580, at least one of cell lysers 537 (in the form of a fluid actuator, such as a thermal resistor) may be actuated while fluid ejectors 434 are not actuated or fired, wherein cell lysers 537 are actuated so as to provide a sufficient fluid displacement force and pressure increased to break the meniscus and open the respective capillary break 550.

Controller 572 is similar to controller 472 in that controller 572 comprises a processing unit and associated instructions that control at least some of the functions carried out on die 422. The processing unit of controller 572 follows such instructions, contain on a non-transitory computer-readable medium, to control fluid actuators 54, to control capillary break opener 489, capillary break opener 496, capillary break opener 492, cell lysers 537 and capillary break openers 552. The processing unit of controller 572 is connected to each of such component through electrically conductive wires or traces on die 422.

In one implementation, controller 572 carries out method 100 described above. In one implementation, controller 572 receives an input indicating when a sample has been introduced into sample preparation zone 530. In other implementations, controller 572 is connected to a sensor 431 that senses the introduction of a sample into sample preparation zone 530. While the sample is within sample preparation zone 530, within slot 533 and passages 535, controller 572 outputs control signals selectively actuating cell lysers 537 to lyse the cells in the sample. In some implementations, lysers 537 may be omitted where chemical or other mechanisms are used to lyse the cells. Following a predetermined lapse of time sufficient to allow nucleic acid separation, isolation and concentration, such as adsorption to beads 476, controller 572 outputs control signals causing actuators 54 to eject non-nucleic acid portions into a diaper, reservoir or another passage.

Upon receiving an input or signal from sensor 431 indicating that the non-nucleic acid portions of the sample have been sufficiently ejected and discharged, controller 572 may output control signals causing capillary break opener 489 to break the menisci of capillary breaks 487 to open valve 465, supplying the wash fluid from supply 464 to sample preparation zone 430. In one implementation, the introduction of the wash fluid 464 may be sensed by sensor 431 and communicated to controller 572. The wash fluid further ensures removal of non-nucleic acid portions of the sample. Controller 572 may output control signals causing fluid actuators 54 to further eject the wash fluid through orifices 52. The wash cycle may be repeated until the preparation zone 530 has been sufficiently washed and cleaned and is emptied.

Following the cleaning of sample preparation zone 430, controller 572 may further output control signals causing capillary break opener 492 to open valve 467, supplying the elution fluid from supply 466 to sample preparation zone 530. The elution fluid releases or elutes the nucleic acid from any nucleic acid retainers/filters/beads. In one implementation, the fluid releases the nucleic acid from the adsorption beads 476.

Upon the release of the nucleic acid from the retainers, such as beads 476, controller 572 outputs control signals causing capillary break opener 498 to open valve 470, supplying a fluid containing the nucleic acid amplification reagent from supply 468 to sample preparation zone 530. The nucleic acid amplification reagent fluid mixes with the nucleic acid in sample preparation zone 530. In implementations where the reagent fluid has a composition so as to release or elutes the nucleic acid from any nucleic acid retainers/filters, such as from the adsorption beads 476, the supplying of the elution fluid from supply 466 through the actuation of valves 467 may be omitted.

The nucleic acid amplification reagent fluid mixes with the nucleic acid in sample preparation zone 430. As noted above, in some implementations, the step may be modified or omitted where amplification regions 580 include freeze-dried nucleic acid amplification reagent 499. In such an implementation, the fluid (provided from supply 468, from sample port 460 or another port or reservoir) may omit nucleic acid amplification reagent, wherein the fluid releases a nucleic acid and carries a nucleic acid into amplification region 480 where the fluid then mixes with the freeze-dried nucleic acid amplification reagent. The volume of the fluid, whether containing nucleic acid amplification reagent or omitting nucleic acid amplification reagents, is controlled so as to substantially, and in one implementation fully, prime amplification region 480 without opening or breaking meniscus across capillary break 486.

Upon mixing of the nucleic acid amplification reagent with the released nucleic acid in preparation zone 530, as determined from signals from sensor 431, controller 572 outputs control signals actuating capillary break openers 452. In one implementation, controller 572 outputs control signals actuating a fluid actuator so as to break the meniscus across each of capillary breaks 550, facilitating the flow of fluid mixture containing the nucleic acid amplification reagent and the nucleic acid into amplification regions 580. In one implementation, sample preparation zone 530 is backfilled with fluid, such as with water, to further inhibit evaporation during thermal cycling.

Upon mixing of the nucleic acid amplification reagent (whether from supply 468 and/or from freeze-dried reagent 499), controller 572 may output control such signals causing heater 482 to thermal cycle the fluid mixture within amplification regions 580. In some implementations, controller 572 may communicate with at least one sensor 433, located within each amplification region 580, which indicates to controller 572 the presence of the fluid mixture in amplification region 580, its state of amplification and/or the current temperature of the fluid mixture. During such thermal cycling, evaporation from the amplification regions 580 is reduced as there are very few vent ports. The meniscus across capillary breaks 584 reduces evaporation through vent 484 whereas the meniscus across capillary break 550, reestablished after priming of the amplification region 480, reduces evaporation through orifices 52.

Upon completion of thermal cycling, the presence and amount, if any, of the targeted nucleic acid is sensed or detected. In one implementation, microfluidic die 422 comprises a window or transparent portions that facilitate optical sensing or detection of the targeted nucleic acid within amplification regions 580. The amplification carried out by amplifier 520 may be utilized to facilitate the isolation or quantification of nucleic acids. Such amplification may offer benefits in such areas as genetic testing, tissue typing, infectious disease identification, genetic fingerprinting and the development of individually customized therapy regimens, forensic analysis, food safety, environmental testing etc.

Figure 7:
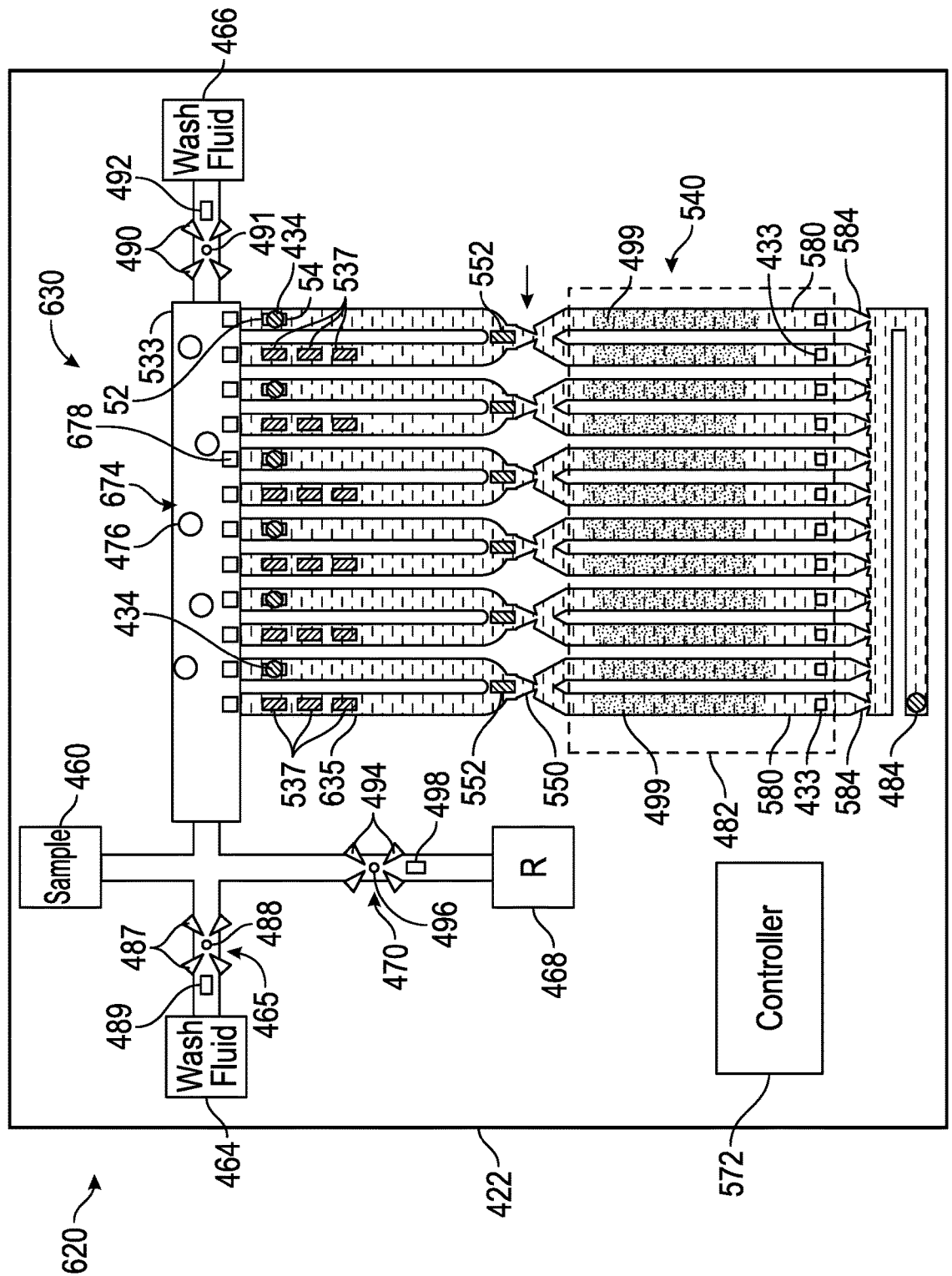
FIG. 7 is a schematic diagram of portions of an example nucleic acid amplifier.

FIG. 7 schematically illustrates portions of an example nucleic acid amplifier 620. Amplifier 620 is similar to amplifier 520 described above except that amplifier 620 comprises sample purification/preparation zone 630. Those remaining components of amplifier 620 which correspond to components of amplifier 520 or amplifier 420 are numbered similarly.

Sample preparation zone 630 comprises an area of microfluidic die 422 where a targeted nucleic acid is separated or isolated from remaining non-nucleic acid portions of a sample introduced through sample supply 460. In the example illustrated, zone 630 comprises an elongate slot 533, a series of U-shaped microfluidic passages 635, nucleic acid separator 674 and cell lysers 537. Slot 533 is connected to sample supply 460, wash fluid supply 464 and nucleic acid amplification reagent supply 468. Both ends of each of microfluidic passages 635 are connected to slot 533, with a first end containing at least one cell lyser 537 and a second opposite end containing a fluid ejector 434.

Nucleic acid separator 674 separator isolates nucleic acid from non-nucleic acid portions of a dilute sample. In one implementation, nucleic acid separator 674 comprises nucleic acid adsorption beads 476 (a portion of which are schematically shown) and adsorption bead retainers 678. Nucleic acid adsorption beads 476 are formed from material or are coated such that a target nucleic acid absorbs to the beads 476. Nucleic acid adsorption beads 476 may reside within zone 630 prior to the addition of a dilute sample or may be added to the dilute sample prior to the introduction of the dilute sample into zone 630. Nucleic acid adsorption beads 476 are retained in slot 533 by retainers 578.

Nucleic acid adsorption bead retainers 678 inhibit the passage of beads 476 (and the absorbed target nucleic acid) from slot 533 to microfluidic passages 635, containing fluid ejectors 434. In the example illustrated, retainers 578 comprise pillars or posts within passages 535, adjacent slot 533. In other implementations, retainers 478 may comprise other forms of a filter which block the passage of beads 476 while permitting the fluid containing non-nucleic acid portions to pass therethrough to passages 635.

In yet other implementations, nucleic acid separator 674 may have other forms. For example, in other implementations, nucleic acid separator 674 may comprise a mesh or other filtering material that adsorbs targeted nucleic acids. In yet other implementations, nucleic acid separator may comprise an embedded membrane. In some implementations, nucleic acid separator 674 may be omitted such as where the diluted sample includes few bacteria such that the nucleic acid may be concentrated through evaporation.

Fluid ejectors 434 dispense or eject the non-nucleic acid portions of the dilute sample separated from the target nucleic acid. Fluid ejectors 434 reside at the end of passages 635. Each of fluid ejectors 434 comprises an orifice 52 and a fluid actuator 54 (described above).

Cell lysers 537 comprise components supported by microfluidic die 422 for lysing the cells contained within the sample introduced through sample supply 460. Cell lysers 537 apply heat and/or agitation to the lysate the cells. In the example illustrated, cell lysers 537 comprise fluid actuators that agitate the fluid. In one implementation, cell lysers 537 comprise thermal resistive fluid actuators that agitate as well as heat the fluid to lyse the cells of the sample. The fluid actuators forming cell lysers 537 are sequentially or consecutively located along each of passages 635. As shown by FIG. 6, the number of cell lysers may vary. The multiple cell lysers 537 sequentially located along each of passages 635 facilitate staged lysing of the cells, wherein the different cell lysers along each individual passage 635 may have different characteristics or may be actuated in different manners by controller 572 depending upon the relative location of the individual cell lysers in the series along each passage 635. In one implementation, the cell lysers are simultaneously actuated or fired. In another implementation, the cell lysers are sequentially actuated or fired.

Cell preparation zone 630 facilitates circulation of a sample from slot 533, through passages 635 and back to slot 533. As the fluid sample is circulated through such passages 635, the fluid sample may undergo repeated cycles of lysation by cell lysers 537. At the same time, the adsorption beads 476 are retained within slot 533, out of the regions where cell lysation is taking place. Once the fluid sample and cells have sufficiently undergone lysing, controller 572 may actuate fluid ejectors 4342 eject the non-nucleic acid portions of the sample. After sample preparation zone 630 has been cleaned with a wash fluid, controller 572 may supply the nucleic acid amplification reagent fluid for mixing with the isolated and concentrated nucleic acid. Thereafter, controller 572 may actuate capillary break openers 552 to open capillary breaks 550 such that the nucleic acid amplification reagent fluid and carried nucleic acid flow into amplification zone 540 for amplification as described above. As described above, in some implementations, capillary break openers 552 may be omitted where cell lysers 537 also serve as capillary break openers.

Figure 8:
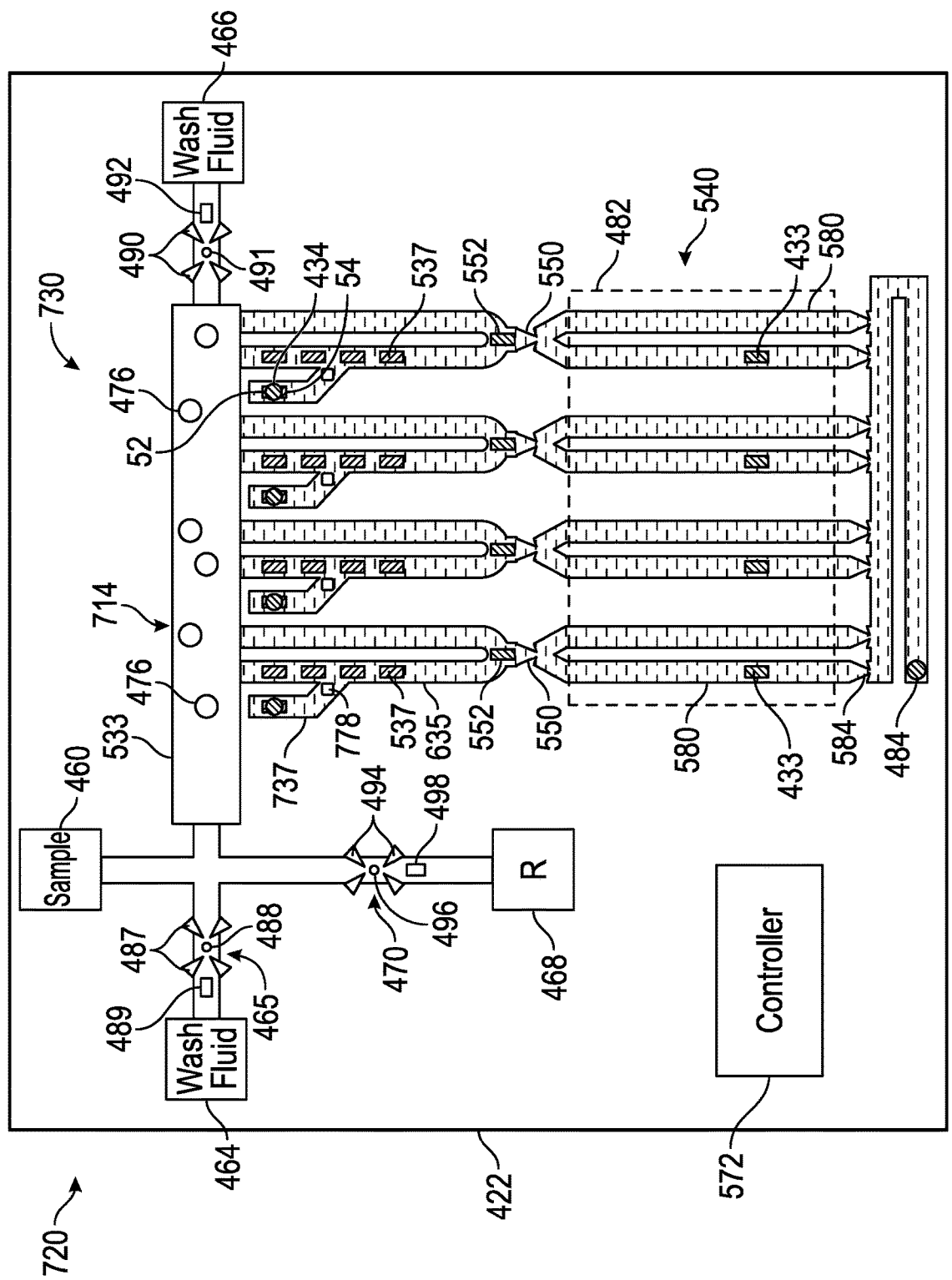
FIG. 8 is a schematic diagram of portions of an example nucleic acid amplifier.

FIG. 8 schematically illustrates portions of an example nucleic acid amplifier 720. Nucleic acid amplifier 720 is similar to nucleic acid amplifier 520 except that nucleic acid amplifier 720 comprises sample purification/preparation zone 730. Those remaining components of amplifier 720 which correspond to components of amplifier 520 are numbered similarly.

Sample preparation zone 730 comprises an area of microfluidic die 422 where a targeted nucleic acid is separated or isolated from remaining non-nucleic acid portions of a sample introduced through sample supply 460. In the example illustrated, zone 730 comprises an elongate slot 533, a series of U-shaped microfluidic passages 635, fluid ejection passages 737, nucleic acid separator 774 and cell lysers 537 (described above). Slot 533 is connected to sample supply 460, wash fluid supply 464 and nucleic acid amplification reagent supply 468. Both ends of each of microfluidic passages 635 are connected to slot 533. Fluid ejection passages 737 branch off of passages 635 and have terminal ends or blind ends. Fluid ejection passages 737 provide areas where fluid may be ejected outside of the recirculation path provided by passages 635.

Nucleic acid separator 774 separates or isolates nucleic acid from non-nucleic acid portions of a dilute sample. In one implementation, nucleic acid separator 774 comprises nucleic acid adsorption beads 476 (a portion of which are schematically shown) and adsorption bead retainers 778. Nucleic acid adsorption beads 476 are formed from material or are coated such that a target nucleic acid adsorbs to the beads 476. Nucleic acid adsorption beads 476 may reside within zone 730 prior to the addition of a dilute sample or may be added to the dilute sample prior to the introduction of the dilute sample into zone 730. Nucleic acid adsorption beads 476 are retained in slot 533 and/or passages 635 by retainers 778 and the constricted regions of capillary breaks 550.

Nucleic acid adsorption bead retainers 778 inhibit the passage of beads 476 (and the adsorbed target nucleic acid) from zone 730 to fluid ejectors 434. In the example illustrated, retainers 778 comprise pillars or posts within passages 737 or at a junction of passages 737 and 635, between portions of passage 635 and fluid ejectors 434, which are positioned within passages 737. In other implementations, retainers 478 may comprise other forms of a filter which block the passage of beads 476 while permitting the fluid containing non-nucleic acid portions to pass therethrough to fluid ejectors 434.

In yet other implementations, nucleic acid separator 774 may have other forms. For example, in other implementations, nucleic acid separator 774 may comprise a mesh or other filtering material that adsorbs targeted nucleic acids within slot 533 or passages 635. In yet other implementations, nucleic acid separator may comprise an embedded membrane. In some implementations, nucleic acid separator 574 may be omitted such as where the diluted sample includes few bacteria such that the nucleic acid may be concentrated through evaporation.

Fluid ejectors 434 dispenser eject the non-nucleic acid portions of the dilute sample separated from the target nucleic acid. Fluid ejectors 434 reside at the end of passages 737, with retainers 778 positioned between fluid ejectors 434 and passages 635. Each of fluid ejectors 434 comprises an orifice 52 and a fluid actuator 54 (described above).

Sample preparation zone 730 facilitates circulation of a sample from slot 533, through passages 635 and back to slot 533. As the fluid sample is circulated through such passages 635, the fluid sample may undergo repeated cycles of lysation by cell lysers 537. At the same time, the adsorption beads 476 are retained within slot 533 and passages 635. Once the fluid sample and cells have sufficiently undergone lysing, controller 572 may actuate fluid ejectors 434 to eject the non-nucleic acid portions of the sample. After sample preparation zone 730 has been cleaned with a wash fluid, controller 572 may supply the nucleic acid amplification reagent fluid for mixing with the isolated and concentrated nucleic acid. Thereafter, controller 572 may actuate capillary break openers 552 to open capillary breaks 550 such that the nucleic acid amplification reagent fluid and carried nucleic acid flow into amplification zone 540 for heating and amplification as described above. As described above, in some implementations, capillary break openers 552 may be omitted where cell lysers 537 also serve as capillary break openers.

Figure 9:
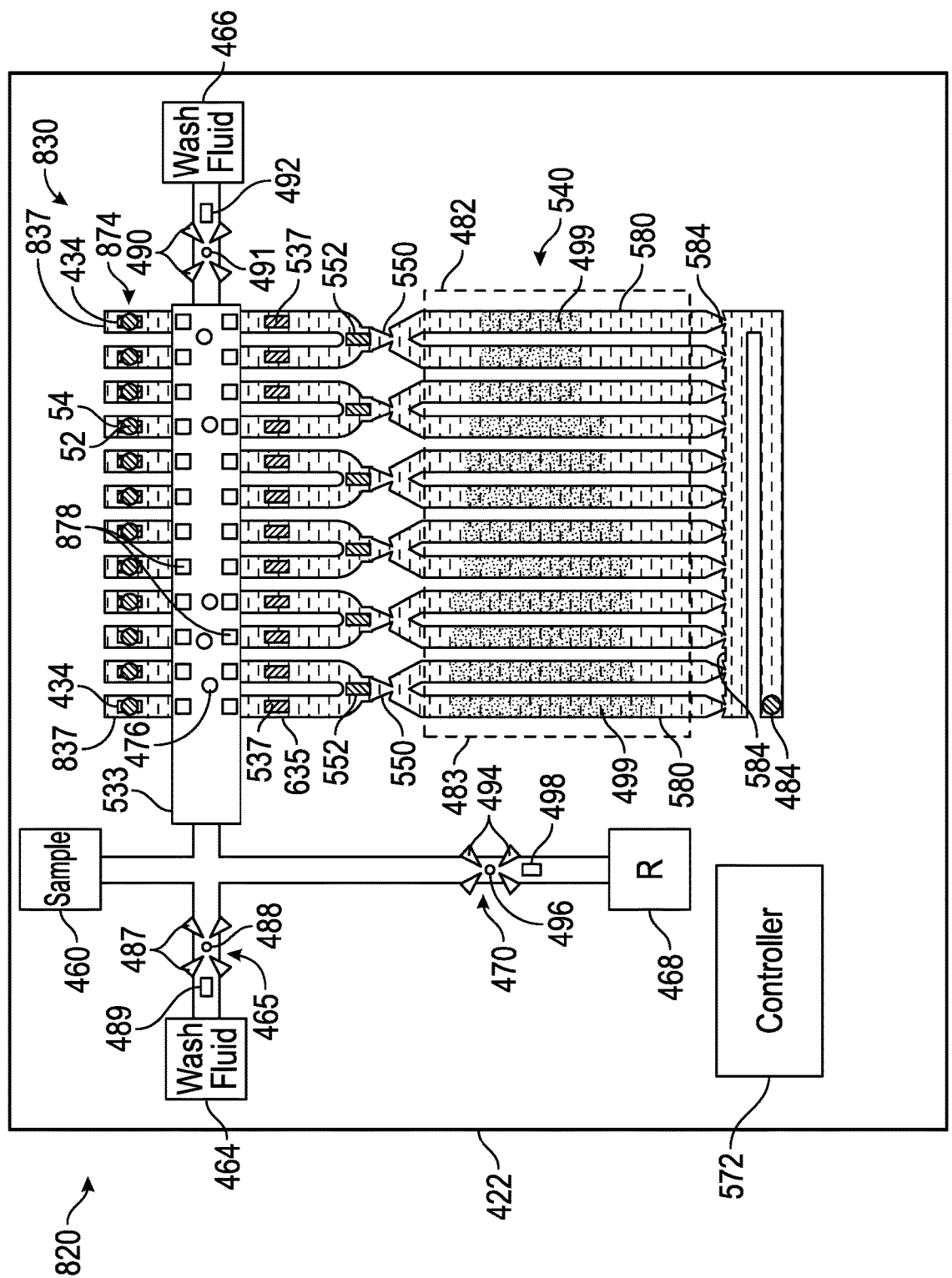
FIG. 9 is a schematic diagram of portions of an example nucleic acid amplifier.

FIG. 9 schematically illustrates portions of an example nucleic acid amplifier 820. Amplifier 820 is similar to amplifier 620 described above except that amplifier 820 comprises sample purification/preparation zone 830. Those remaining components of amplifier 820 which correspond to components of amplifier 620 or other disclose amplifiers are numbered similarly.

Sample preparation zone 830 comprises an area of microfluidic die 422 where a targeted nucleic acid is separated or isolated from remaining non-nucleic acid portions of a sample introduced through sample supply 460. In the example illustrated, zone 830 comprises an elongated slot 533, a series of U-shaped microfluidic passages 635, fluid ejection passages 837, nucleic acid separator 874 and cell lysers 537. Slot 533 is connected to sample supply 460, wash fluid supply 464 and nucleic acid amplification reagent supply 468. Both ends of each of microfluidic passages 635 are connected to slot 533.

Fluid ejection passages 837 extend from slot 533 on an opposite side of slot 533 as passages 635. Fluid ejection passages 837 provide areas where fluid may be ejected outside of the recirculation path provided by passages 635. Fluid ejection passages 837 contains fluid ejectors 434. Because fluid ejection passages 837 extend along an opposite side of slot 533, fluid passages 837, and the fluid ejectors 434 that reside therein, are further isolated and are remotely located with respect to nucleic acid amplification zone 540 to further reduce evaporation that may occur during the thermal cycling in zone 540.

Nucleic acid separator 874 separates or isolates nucleic acid from non-nucleic acid portions of a dilute sample. In one implementation, nucleic acid separator 874 comprises nucleic acid adsorption beads 476 (a portion of which are schematically shown) and adsorption bead retainers 878. Nucleic acid adsorption beads 476 are formed from material or are coated such that a target nucleic acid adsorbs to the beads 476. Nucleic acid adsorption beads 476 may reside within zone 830 prior to the addition of a dilute sample or may be added to the dilute sample prior to the introduction of the dilute sample into zone 830. Nucleic acid adsorption beads 476 are retained in slot 533 by retainers 878.

Nucleic acid adsorption bead retainers 878 inhibit the passage of beads 476 (and the adsorbed target nucleic acid) from slot 533 to fluid ejectors 434. In the example illustrated, retainers 878 comprise pillars or posts within slot 533 located between slot 533 and fluid ejectors 434, such as within passages 837, within slot 533 or at a junction of passages 837 and slot 533. In other implementations, retainers 478 may comprise other forms of a filter which block the passage of beads 476 while permitting the fluid containing non-nucleic acid portions to pass therethrough to fluid ejectors 434.

In yet other implementations, nucleic acid separator 774 may have other forms. For example, in other implementations, nucleic acid separator 874 may comprise a mesh or other filtering material that adsorbs targeted nucleic acids within slot 533. In yet other implementations, nucleic acid separator may comprise an embedded membrane. In some implementations, nucleic acid separator 874 may be omitted such as where the diluted sample includes few bacteria such that the nucleic acid may be concentrated through evaporation.

Fluid ejectors 434 dispenser eject the non-nucleic acid portions of the dilute sample separated from the target nucleic acid. Fluid ejectors 434 reside at the end of passages 837, with retainers 778 positioned between fluid ejectors 434 and slot 533. Each of fluid ejectors 434 comprises an orifice 52 and a fluid actuator 54 (described above).

Sample preparation zone 730 facilitates circulation of a sample from slot 533, through passages 635 and back to slot 533. As the fluid sample is circulated through such passages 635, the fluid sample may undergo repeated cycles of lysation by cell lysers 537. At the same time, the adsorption beads 476 are retained within slot 533. Once the fluid sample and cells have sufficiently undergone lysing, controller 572 may actuate fluid ejectors 434 to eject the non-nucleic acid portions of the sample. After sample preparation zone 830 has been cleaned with a wash fluid, controller 572 may supply the nucleic acid amplification reagent fluid for mixing with the isolated and concentrated nucleic acid. Thereafter, controller 572 may actuate capillary break openers 552 to open capillary breaks 550 such that the nucleic acid amplification reagent fluid and carried nucleic acid flow into amplification zone 540 for heating and amplification as described above. As described above, in some implementations, capillary break openers 552 may be omitted where cell lysers 537 also serve as capillary break openers.

Although the present disclosure has been described with reference to example implementations, workers skilled in the art will recognize that changes may be made in form and detail without departing from the spirit and scope of the claimed subject matter. For example, although different example implementations may have been described as including one or more features providing one or more benefits, it is contemplated that the described features may be interchanged with one another or alternatively be combined with one another in the described example implementations or in other alternative implementations. Because the technology of the present disclosure is relatively complex, not all changes in the technology are foreseeable. The present disclosure described with reference to the example implementations and set forth in the following claims is manifestly intended to be as broad as possible. For example, unless specifically otherwise noted, the claims reciting a single particular element also encompass a plurality of such particular elements. The terms "first", "second", "third" and so on in the claims merely distinguish different elements and, unless otherwise stated, are not to be specifically associated with a particular order or particular numbering of elements in the disclosure.

What is claimed is:

1. A nucleic acid amplifier comprising:
    a sample preparation zone;
    a fluid ejector comprising an orifice and a fluid actuator to eject fluid through the orifice;
    an amplification zone; and
    a channel coupled to the sample preparation zone and the amplification zone, the channel comprising a capillary break coupling the amplification zone to the sample preparation zone, the capillary break defined by a constricted dimension of the channel configured to inhibit flow of fluid until a predetermined fluid pressure is applied, the capillary break configured to be broken via a capillary break opener configured to generate the predetermined fluid pressure, the capillary break opener comprising a second fluid actuator.

2. The nucleic acid amplifier of claim 1, wherein the fluid ejector ejects at least a portion of a sample through the orifice.

3. The nucleic acid amplifier of claim 1, wherein the fluid ejector is configured to selectively eject fluid containing non-nucleic acid portions of the sample through the orifice and out of the sample preparation zone.

4. The nucleic acid amplifier of claim 1, wherein the capillary break is a first capillary break, and wherein the amplification zone comprises:
    a thermal processing region;
    a vent port; and
    a second capillary break between the thermal processing region and the vent port, wherein the first capillary break is between the sample preparation zone and the thermal processing region.

5. The nucleic acid amplifier of claim 4 further comprising a freeze-dried nucleic acid amplification reagent in the thermal processing region.

6. The nucleic acid amplifier of claim 4 further comprising a nucleic acid separator within the sample preparation zone.

7. The nucleic acid amplifier of claim 6 further comprising a third fluid actuator between the nucleic acid separator and the second capillary break.

8. The nucleic acid amplifier of claim 6 further comprising a third fluid actuator in the sample preparation zone, wherein the nucleic acid separator is between the second fluid actuator and the first capillary break.

9. The nucleic acid amplifier of claim 8 further comprising a fourth fluid actuator between the second fluid actuator and the first capillary break, wherein the second fluid actuator is proximate a nucleic acid adsorption bead filter and wherein the fourth fluid actuator is proximate the first capillary break.

10. The nucleic acid amplifier of claim 6, wherein the nucleic acid separator comprises nucleic acid adsorption beads and adsorption bead retainers within the sample preparation zone.

11. The nucleic acid amplifier of claim 10, further comprising a cell lyser in the sample preparation zone, wherein the cell lyser comprises a third fluid actuator, and wherein the adsorption bead retainers are between the cell lyser and the first capillary break.

12. The nucleic acid amplifier of claim 11, wherein the capillary break opener is positioned between the cell lyser and the first capillary break, the cell lyser is proximate the nucleic acid adsorption bead retainer, and the capillary break opener is proximate the first capillary break.

13. The nucleic acid amplifier of claim 4, further comprising a microfluidic chip, wherein the sample preparation zone and the amplification zone are located on the microfluidic chip, the nucleic acid amplifier further comprising:
- a wash fluid reservoir on the microfluidic chip and fluidly connected to the sample preparation zone;
- a third capillary break between the wash fluid reservoir and the sample preparation zone; and
- a third fluid actuator between the wash fluid reservoir and the third capillary break.

14. The nucleic acid amplifier of claim 13 further comprising:
- a nucleic acid amplification reagent reservoir on the microfluidic chip and fluidly connected to the sample preparation zone;
- a fourth capillary break between the nucleic acid amplification reagent reservoir and the sample preparation zone; and
- a fourth fluid actuator between the nucleic acid amplification reagent reservoir and the fourth capillary break.

* * * * *